United States Patent [19]

Ohnishi et al.

[11] 4,232,223
[45] Nov. 4, 1980

[54] GAS ANALYZER

[75] Inventors: Toshikazu Ohnishi; Kozo Ishida; Osamu Saitoh, all of Miyanohigashi, Japan

[73] Assignee: Horiba, Ltd., Kyoto, Japan

[21] Appl. No.: 49,971

[22] Filed: Jun. 19, 1979

[30] Foreign Application Priority Data

Oct. 18, 1978 [JP] Japan ................................. 53-128756

[51] Int. Cl.² ............................................. G01N 21/26
[52] U.S. Cl. ..................................... 250/343; 250/345; 250/373
[58] Field of Search ............... 250/343, 344, 345, 373; 251/129, 210, 304

[56] References Cited

U.S. PATENT DOCUMENTS

| 2,674,696 | 4/1954 | Smith et al. | 250/345 |
| 2,709,751 | 5/1955 | Meyer | 250/345 |
| 3,725,702 | 4/1973 | Schaefer | 250/345 X |

*Primary Examiner*—Davis L. Willis
*Attorney, Agent, or Firm*—Wenderoth, Lind & Ponack

[57] ABSTRACT

A gas analyzer for measuring the concentration of a gaseous component in a test gas includes first and second separate cells adapted to alternately be filled with a test gas containing a gaseous component to be analyzed and a standard gas, light sources for directing rays of energy through the first and second cells and through the test gas and standard gas alternately contained therein, a detector positioned to receive the rays of energy after passage thereof through the first and second cells for detecting the concentration of the gaseous component within the test gas, and a changeover device connected to the first and second cells and adapted to be connected to sources of the test gas and the standard gas for alternately supplying the test gas and standard gas, at fixed intervals and in fixed amounts, into the first and second cells. The changeover device includes a single block having therein first and second inlets adapted to be connected to the source of test gas and the source of standard gas, respectively, first and second outlets respectively connected to the first and second cells, and a rotary valve rotatably movable between a first position respectively connecting the first and second inlets with the first and second outlets and a second position respectively connecting the first and second inlets with the second and first outlets.

5 Claims, 11 Drawing Figures

GAS ANALYZER

BACKGROUND OF THE INVENTION

The present invention relates to gas analyzers, such as an infrared ray gas analyzer of the non-dispersion type or an ultraviolet ray gas analyzer of the non-dispersion type which are used for measuring the concentration of carbon monoxide or the like in air.

Conventional infrared gas analyzers of the non-dispersion type are shown in FIG. 1 and FIG. 2. FIG. 1 shows a gas analyzer of the non-dispersion type which employs a double light path and intermittent light and which includes light source or sources 44, revolving sector 45, reference cell 46, measurement cell 47 and detector 41. Although various types of detectors have been used, a pneumatic detector employing a condenser microphone will be described herein. In order to eliminate the influence of changes in the surrounding temperature upon detector 41, separate right and left chambers 42 are provided with connecting leak opening 43 therebetween, so that there will always be a static pressure equilibrium therebetween. Thus, detector 41 can sense only dynamical pressures having short cycles. In order to realize this, revolving sector 45 is provided which intermittently emits infrared rays from light source 44 at constant intervals. Furthermore, gases such as nitrogen which do not absorb infrared rays are enclosed in a reference cell 46. Zero gas is put into a sampling cell 47, and then the energy of infrared rays reaching the respective chambers 42 of detector 41 is kept balanced, and moreover their phases are so equalized that the output of detector 41 may be adjusted to zero. Then, a test gas is introduced into sampling cell 47. If the test gas absorbs the energy of the infrared rays passing through sampling cell 47, a difference will occur between the energy of infrared rays which pass through sampling cell 47 and the energy of infrared rays which pass through reference cell 46. This difference of energy levels leads to the generation of an unbalanced pressure signal synchronized with the cycles of revolving sector 45 between the respective chambers 42 of detector 41. The concentration of a specified gaseous component in the test gas can be measured by the indication of an indicator 47 against an amplified such pressure signal.

However, in this method a slight break in energy balance between the respective chambers 42 of the optical system operates to negate the high degree of stability necessary in a high sensitive region. This is the reason why this method is not suitable for measuring gaseous components of particularly small amounts. Because a remarkably high precision in the balance of energy is required, zero adjustment of detector 41 to achieve equalization of phases is necessary, and such adjustment is troublesome and time-consuming. Furthermore, expensive apparatus is required for carrying out such adjustment. In addition, there also exists the problem of maintenance, since the device includes mechanically movable parts.

FIG. 2 shows a single light path gas analyzer of the non-dispersion type in which the intermittent light method is employed without using the reference cell and the revolving sector described in the above mentioned example. In this arrangement, 51 is a sampling cell and 58 is a detector. Although various types of detectors have been used, a pneumatic detector will be described herein. The test gas and the standard gas (for example, zero gas) are alternately introduced into sampling cell 51 by operating pressure regulators 53a and 53b and needle valves 54a and 54b, respectively, and by alternately opening and closing three-way electromagnetic valves 52a and 52b. At first infrared rays emitted from a light source 55 are not absorbed while sampling cell 51 is filled with zero gas. On the other hand, the special gaseous component in a test gas absorbs infrared rays while the test gas is introduced int sampling cell 51. Thus, a condenser membrane 57 provided in the separated chamber 56 is pressurized, and the static capacity of the condenser is altered at a constant cycle synchronized with a changeover cycle of three-way electromagnetic valves 52a and 52b. The concentration of the gaseous component is measured by electrically measuring such change in the static capacity of the condenser.

But, although this single-cell type of arrangement can overcome the defects of the above mentioned gas analyzer of FIG. 1 to some degree, the length of the sampling cell is increased in order to measure the special gaseous components which are contained in the test gas in a specially small amount because the quantity of infrared rays absorbed is in proportion to the length of the cell, and thus also the space for receiving gas in sampling cell 51 is increased. Therefore, the quantity of the test gas or zero gas introduced into sampling cell 51 is increased enormously in the measurement of gaseous components of a small amount. For example, in the measurement of carbon monoxide in air, the length L of cell 51 must be 30 to 50 cm, and the space V for receiving gas must be 90 to 150 cm$^3$. If a frequency of 5 Hz is used in detector 58, the test gas or zero gas must be introduced into sampling cell 51 at a ratio of 27 to 45 liters/min. Thus, a pump of a great capacity is required and therefore a large scale apparatus is required. This leads to the problem of high costs. A gas analyzer of this type has a defect in that it has no practical use because a supply of zero gas of great volume is required in addition to the above mentioned troublesome problems.

SUMMARY OF THE INVENTION

The object of the present invention is to provide a gas analyzer which can measure special gaseous components in a test gas with a remarkable precision due to its high stability and good operability, and in particular can effectively measure gaseous components of a small amount in order to overcome the disadvantages of the above mentioned gas analyzers.

Another object of the present invention is to provide a gas analyzer wherein in particular the changing over portion of the gas flowing path has a small dead space, the replacement of the gas can be carried out by supplying a comparatively small amount of gas, and a compact construction is possible.

The above objects are achieved in accordance with the present invention by the provision of a gas analyzer including first and second separate cells adapted to alternately be filled with a test gas containing a gaseous component to be analyzed and measured and a standard gas. A light source or sources direct rays of energy, for example infrared rays or ultraviolet rays, through the first and second cells and through the test gas and standard gas alternately contained therein. A detector, for example of the pneumatic type including a condenser microphone, is positioned to receive the rays of energy after passage thereof through the first and second cells, for thereby detecting the concentration of the gaseous component within the test gas.

In accordance with a particularly novel feature of the present invention, there is provided a changeover device, connected to the first and second cells and adapted to be connected to sources of the test gas and the standard gas, for alternately supplying the test gas and the standard gas, at fixed intervals and in fixed amounts, into the first and second cells. The changeover device preferably comprises a single block having therein first and second inlets adapted to be connected to the source of test gas and the source of standard gas, respectively, first and second outlets respectively connected to the first and second cells, and a rotary valve movable between a first position respectively connecting the first and second inlets with the first and second outlets and a second position respectively connecting the first and second inlets with the second and first outlets.

In accordance with one embodiment of the present invention, the rotary valve includes a motor mounted on the block and having a rotatable output shaft, and a valve member directly coupled to the rotatable output shaft.

In accordance with a modified embodiment of the present invention, the rotary valve device comprises a motor mounted on the block and having a rotatable output shaft, a magnet connected to the output shaft and rotatable therewith, a valve member positioned within the block, and a rotary plate made of a magnetic material and connected to the valve member, such that the rotary plate and thus the valve member are indirectly rotated by the magnet due to the magnetic force thereof.

BRIEF DESCRIPTION OF THE DRAWINGS

Other objects and advantages of the invention will be apparent from the following description, taken with the accompanying drawings, wherein.

DETAILED DESCRIPTION OF THE INVENTION

The infrared gas analyzer of the invention will now be explained with reference to FIGS. 3 through 8.

Figure 3:
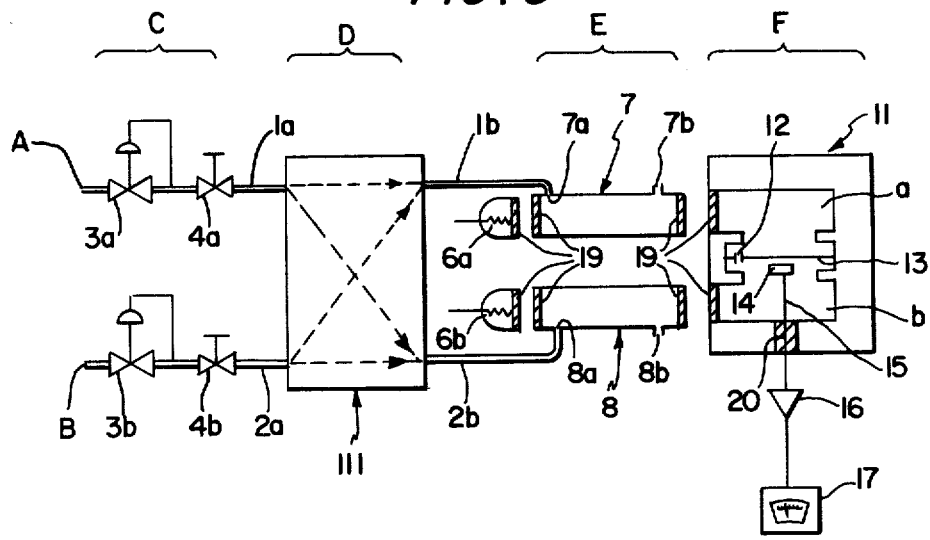
FIG. 3 is a schematic view of a first embodiment of the invention.

FIG. 3 schematically shows a fisrt embodiment of the invention, wherein the test gas and the standard gas are introduced into a cell portion E including a first cell 7 and a second cell 8 and then are detected in a detecting portion F, after passing through an introducing portion C and a flow path changeover portion D and being subjected to changeover at constant intervals.

Explaining the above in more detail, pressure regulators 3a and 3b and needle valves 4a and 4b are arranged in series in first upstream gas flow path 1a and second upstream gas flow path 2a having inlets A and B, respectively. First downstream gas flow path 1b and second downstream gas flow path 2b are connected with inlets 7a and 8a of the first cell 7 and the second cell 8, respectively. Cells 7 and 8 have respective outlets 7b and 8b. Flow path changeover portion D includes a changeover block 111 provided between the gas flow paths 1a and 2a and the gas flow paths 1b and 2b.

The analyzer unit includes a detector 11, an amplifier 16 and an indicator 17. The detector 11 must be a suitable detector selected depending on the type of light to be detected. For example, an infrared detector is used for infrared rays and an ultraviolet detector is used for ultraviolet rays. An infrared detector will be explained with reference to the illustrated embodiment of FIG. 3. Although the infrared detector may be a solid detector in which a pyroelectric couple, a semiconductive couple, a thermoelectric couple or the like is used, the discussion hereinafter will be of a pneumatic detector in which a condenser microphone is used. A condenser membrane 13 having a leak 12 therein is provided as one condenser plate or pole and defines separate chambers a and b which receive the rays from light sources 6a and 6b, respectively, through cells 7 and 8, respectively. A fixed plate or pole 14 is arranged as the other plate of the condenser at a position facing condenser membrane 13. Fixed pole 14 is connected with amplifier 16 and indicator 17 through a lead wire 15, insulated as at 20. Windows 19, transparent to the particular rays employed, are provided in light sources 6a and 6b, in cells 7 and 8 and in chambers a and b.

In such construction, a test gas and a standard gas (for example, a zero gas such as nitrogen or the like) are continuously introduced into the analyzer from inlet A and inlet B, respectively. Initially, by suitably adjusting the flow path changeover portion D, the gas flow path 1a is connected to the gas flow path 1b, and simultaneously the gas flow path 2a is connected to the gas flow path 2b. As a result, the test gas and zero gas are introduced and filled into first cell 7 and second cell 8, respectively. Then, by changing the flow path changeover portion D, the gas flow path 1a is connected to the gas flow path 2b, and simultaneously the gas flow path 1b is connected to the gas flow path 2a. As a result, the test gas and zero gas are introduced into second cell 8 and first cell 7, respectively. Thus, the test gas and zero gas are alternately filled into first cell 7 and second cell 8 through inlets 7a and 8a, respectively, and are alternately discharged from first cell 7 and second cell 8 outside of the analyzer through exits 7b and 8b, respectively. At this time, the amounts of the supplied test gas and zero gas are fixedly regulated by pressure regulators 3a and 3b and needle valves 4a and 4b, respectively. Furthermore, the changeover cycle of flow path changeover portion D is regulated by a controller (not shown) so that it may be equalized with the frequency of the detector.

Figure 4A:
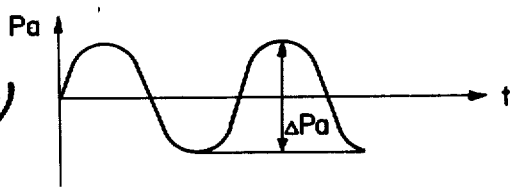
FIGS. 4(a), 4(b) and 4(c) are graphs showing the output of the detector.
Figure 4B:
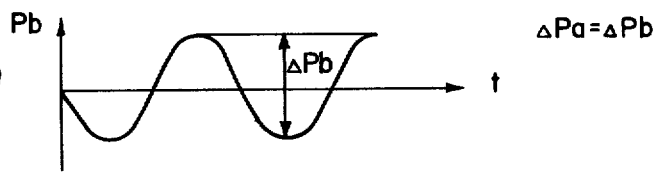

If zero gas is introduced simultaneously into both cells 7 and 8, infrared rays emitted from light sources 6a and 6b are not absorbed and therefore detector 11 shows a zero output. However, as the different gases are alternatively filled into both cells 7 and 8 at fixed intervals and in fixed amounts by the repetition of the above mentioned operations, the energy of infrared rays is absorbed by the special gaseous components contained in the test gas, alternately in first cell 7 and second cell 8, in the same manner as in a gas analyzer of the single cell type. Thus, the pressure Pa inside separate chamber a of detector 11 will vary as shown in FIG. 4(a), wherein t is time and Pa is pressure, while the pressure Pb inside separate chamber b will vary as shown in FIG. 4(b), because the zero gas and the test gas are alternatively introduced into first cell 7 and second cell 8.

Figure 4C:
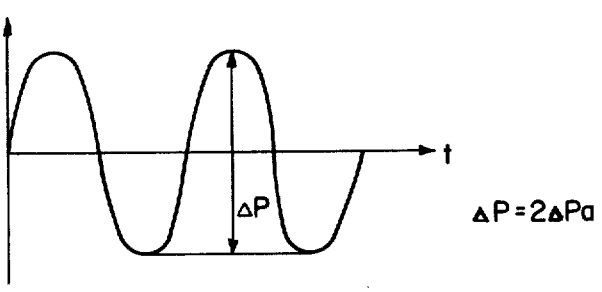

Furthermore, the amplitude or displacements of pressures Pa and Pb are equalized at a phase difference of one-half cycle. Therefore, the pressure acting on condenser membrane 13 is a difference between the pressure Pa inside separate chamber a and the pressure Pb inside separate chamber b, i.e. P=Pa−Pb, as shown in FIG. 4(c). This pressure difference causes an alteration in the static capacity of the condenser, and such alteration is transformed into an electric signal indicative of the concentration of the special gaseous component contained in the test gas. Such electric signal can be amplified by amplifier 16 and read by indicator 17.

Figure 7A:
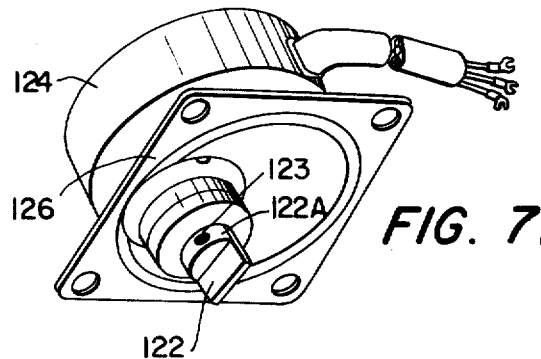
FIGS. 7(a) and 7(b) are perspective views of the elements of the device of FIG. 6.
Figure 7B:
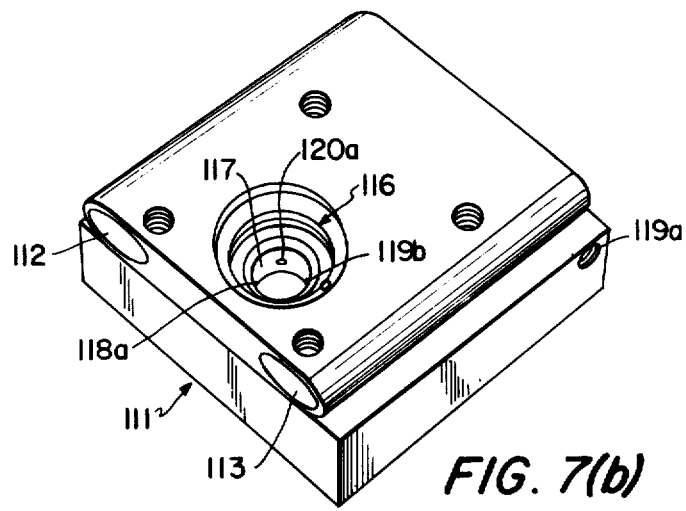
Figure 5:
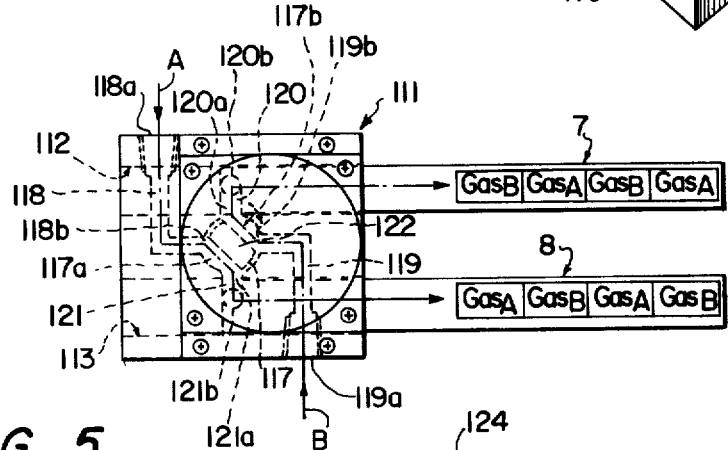
FIG. 5 is a plan view of an example of a block employed in the device of the invention.
Figure 6:
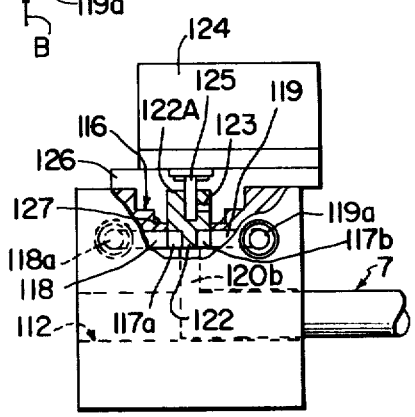
FIG. 6 is a partly sectioned side view of the device of FIG. 5.

The block 111 which forms the gas flow path changeover portion D will now be described. Referring now to FIGS. 5 through 7, block 111 has therein openings 112 and 113. The inlet ends of a pair of cells 7 and 8 are inserted into openings 112 and 113, respectively. Block 111 also has therein an opening 116 for installing a valve which extends orthogonally between openings 112 and 113. Opening 116 is provided at the bottom or inner portion thereof with a gas flow path changeover chamber 117.

Block 111 is provided with four internal gas flow paths or passages 118, 119, 120 and 121. One end of gas flow path 118 opens on one side of block 111, at inlet wall 118a, for example, for connection to flow path 1a for a supply of test gas A. The other end of gas flow path 118 opens into the inside peripheral wall of gas flow path changeover chamber 117, at outlet 118b, as an exit for the test gas A. Furthermore, one end of gas flow path 119 opens on another side of block 111, at inlet 119a, for example, for connection to flow path 2a for the supply of standard gas B. The other end of gas flow path 119 opens into the inside peripheral wall of gas flow path changeover chamber 117, at outlet 119b, as an exit for the standard gas B. On the other hand, first ends of gas flow paths 120 and 121 open into the inside peripheral wall of gas flow path changeover chamber 117, at 120a and 121a, respectively, as outlets for gases A or B toward cells 7 and 8, respectively. The other ends of gas flow paths 120 and 121 form inlets 120b and 121b, respectively, into cells 7 and 8, respectively.

A rotary valve 122 formed on the lower portion of a housing 122A is rotated so that opposite lateral sides thereof are in contact with the inside peripheral surface or wall of gas flow path changeover chamber 117. The housing 122A of valve 122 is fixed on a revolving axis 125 of a synchronous motor 124 by means such as a fastening screw 123. Synchronous motor 124 is fixed on an installing cover 126 positioned in opening 116. O-ring 127 seals chamber 117.

When rotary valve 122 is in the position shown in FIG. 5, the test gas A introduced into inlet 118a passes through gas flow path 118, is discharged from outlet 118b into connecting chamber 117a of gas flow path changeover chamber 117, and then is introduced into cell 8 after passing through outlet 121a, gas flow path 121 and inlet 121b. On the other hand, the standard gas B supplied into inlet 119a passes through gas flow path 118, is discharged from outlet 119b into gas connecting chamber 117b of flow path changeover chamber 117, and then is supplied into cell 7 after passing through outlet 120a, gas flow path 120 and inlet 120b.

Then, rotary valve 122 is rotated, e.g. in a clockwise direction, by 90° from the position shown in FIG. 5, to thus interrupt communication between gas flow paths 118 and 121 as well as between gas flow paths 119 and 120, by action of synchronous motor 124, and to form communication between gas flow paths 118 and 120 as well as between gas flow paths 119 and 121. Thus, the test gas A supplied into inlet 118a is introduced into cell 7, and the standard gas supplied into inlet 119a is introduced into cell 8. Therefore, rotary valve 122 is further rotated by 90°, e.g. in the clockwise direction, such that the valve will be in the same position shown in FIG. 5. As a result, the standard gas B and the test gas A are again supplied into cells 7 and 8, respectively. Rotary valve 122 is intermittently rotated 90° in the above mentioned manner by the action of synchronous motor 124, and as a result the test gas and the standard gas are alternately supplied into cells 7 and 8, respectively.

Figure 1:
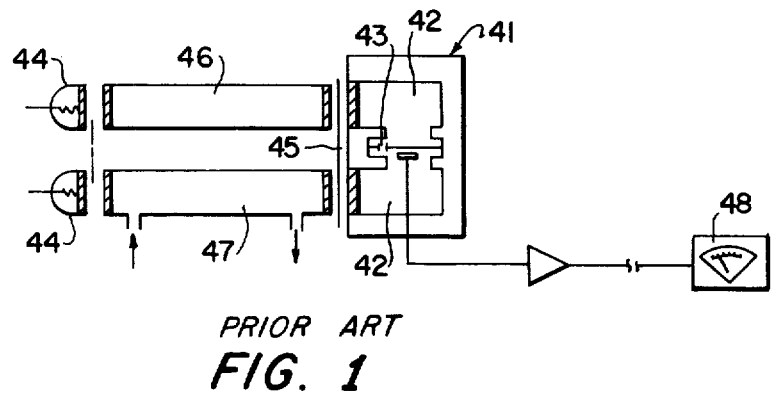
FIGS. 1 and 2 are schematic views of conventional gas analyzers.
Figure 2:
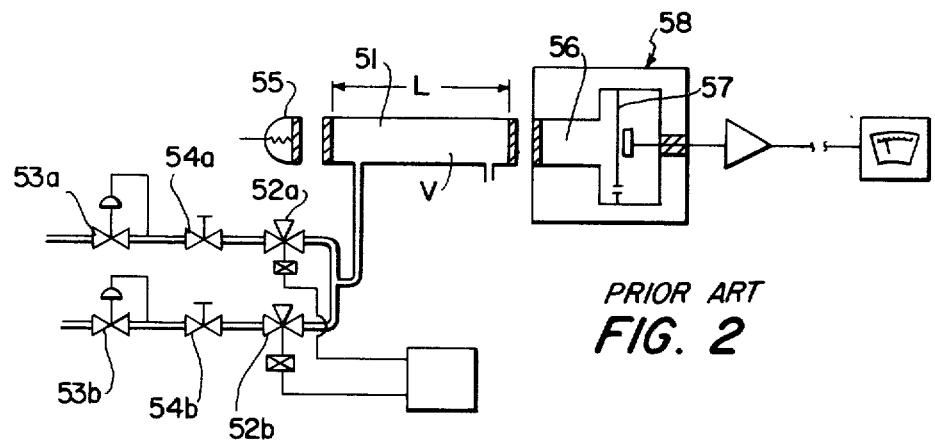
Figure 8:
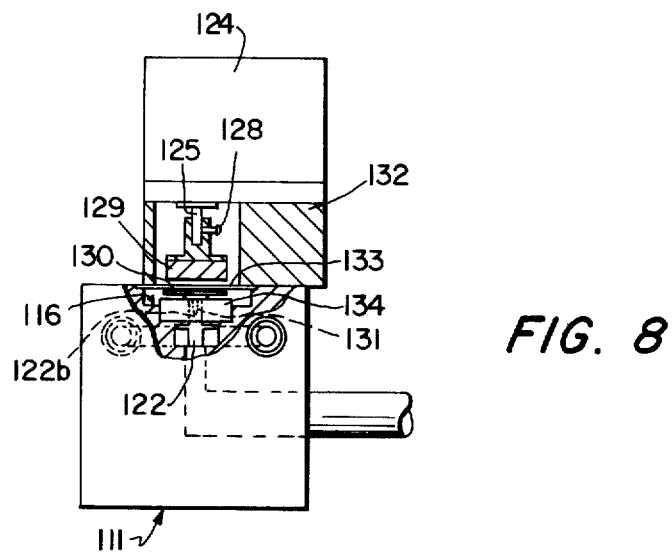
FIG. 8 is a partly sectioned view of another example of a block employed in the device of the invention.

FIG. 8 illustrates a modified embodiment of the gas flow path changeover portion of the invention. That is, in the embodiment of FIGS. 5—7, rotary valve 122 is rotated directly through revolving axis 125 by the rotation of synchronous motor 124. However, according to the embodiment shown in FIG. 8 a magnet 129 is fixed on revolving axis 125 of synchronous motor 124 by a pin 128 and is rotated thereby. The magnetic force of magnet 129 rotates, for example, a revolving plate 130 made of iron positioned within opening 116. Revolving plate 130 and rotary valve 122 are synchronously rotated by synchronous motor 124, because revolving plate 130 is fixed to rotary valve 122 by a screw 131 at an upper end portion of axis 122b of valve 122. In this way, synchronous motor 124 indirectly rotates rotary valve 122 through magnet 129 and revolving plate 130. The arrangement of FIG. 8 also includes a spacer 132, a blank plug 133 and a bearing 134, as shown. The other features of the embodiment of FIG. 8, including construction and the changeover operation of the gas flow paths, are the same as those described above with reference to the embodiment of FIGS. 5 through 7, and therefore further description thereof will not be made herein.

In the above described embodiments of the invention, the end portions of cells 7 and 8 are inserted into openings 112 and 113, respectively, of block 111. However, it is to be understood that the cells themselves may be provided within block 111.

Furthermore, the above described embodiments are made with reference to the use of infrared rays. However, it is to be understood that ultraviolet rays may also be used in the analyzer of the present invention, in which case windows which pass ultraviolet rays would replace windows 19 which pass infrared rays. Also, detector 11 may be of the mass-flow type or the solid type rather than of the pneumatic type described. Additionally, only one light source may be employed, rather than the two sources described.

The above mentioned construction of the invention leads to the following effects.

The test gas and the standard gas are introduced into two cells at fixed intervals and in fixed amounts, and as a result the pressures Pa and Pb occur in the separate chambers of the detector, and the difference between Pa and Pb, that is to say (Pa-Pb), acts on the condenser membrane. At this time, as clearly shown in FIGS. 4(a) through 4(c), the difference (Pa-Pb) between the pressures will double the strength of the resultant signal for an identical concentration of the particular gaseous component detected, as compared with conventional gas analyzers, because the amounts of displacement of pressures Pa and Pb are identical, and because pressures Pa and Pb are out of phase by exactly one-half cycle. In other words, the gas analyzer according to the present invention has a wider range of measurement than conventional analyzers in which a low concentration of a particular gaseous component can be stably measured.

Furthermore, in accordance with the invention, the lengths of the cells can be reduced to half the cell lengths necessary in conventional analyzers for the identical concentration of the particular gaseous component, and thus the overall apparatus can be miniaturized or reduced in size. In addition, the size of the space required for receiving the gases in the cells and the amount of the test gas and the standard gas to be introduced into the cells can be reduced by one-half, and thus the pump for transferring gas also can be miniaturized and reduced in capacity. Accordingly, the gas analyzer of the present invention has much greater ability to measure the content of a gaseous component present in only small amounts in the test gas, for example in the measurement of the concentration of noxious gases contained in the air. Furthermore, the supply of a great volume of the standard or zero gas is not required, and therefore the gas analyzer of the present invention is remarkably superior to conventional analyzers with regard to practical use.

Also, the incorporation of a rotary valve in a single block body for changing over the gas flow paths results in lead reduction of the dead space between the valve and the cell, as compared with a conventional gas analyzer using an electromagnetic valve.

In addition to the above advantages, since according to the invention the displacement of gas can be carried out by supplying comparatively small amounts of gas, the prior art disadvantages of heat and vibration, which are inherent with the use of an electromagnetic valve and which have a harmful influence upon the gas analyzer, can be eliminated. Also, the analyzer of the invention can be more compactly constructed due to the elimination of the need for a unit for driving an electromagnetic valve. Thus, according to the present invention the measurement operation can be achieved more accurately, the gas analyzer can be manufactured more inexpensively, and the gas analyzer will have a longer life.

Although the present invention has been described and illustrated with respect to specific preferred structural features thereof, it will be apparent that various modifications may be made to such specific structural features without departing from the scope of the present invention.

What we claim is:

1. A gas analyzer for measuring the concentration of a gaseous component in a test gas, said gas analyzer comprising:

first and second separate cells adapted to alternately be filled with a test gas containing a gaseous component to be analyzed and a standard gas;

light source means for directing rays of energy through said first and second cells and through the said test gas and standard gas alternately contained therein;

detector means, positioned to receive said rays of energy after passage thereof through said first and second cells, for detecting the concentration of said gaseous component within said test gas; and changeover means, connected to said first and second cells and adapted to be connected to sources of said test gas and said standard gas, for alternately supplying said test gas and said standard gas, at fixed intervals and in fixed amounts, into said first and second cells, said changeover means comprising a single block having therein first and second inlets adapted to be connected to said source of test gas and said source of standard gas, respectively, first and second outlets respectively connected to said first and second cells, and rotary valve means movable between a first position respectively connecting said first and second inlets with said first and second outlets and a second position respectively connecting said first and second inlets with said second and first outlets.

2. A gas analyzer as claimed in claim 1, wherein said rotary valve means comprises a motor mounted on said block and having a rotatable output shaft, and a valve member directly coupled to said rotatable output shaft.

3. A gas analyzer as claimed in claim 1, wherein said rotary valve means comprises a motor mounted on said block and having a rotatable output shaft, a magnet connected to said output shaft and rotatable therewith, a valve member positioned within said block, and a rotary plate made of a magnetic material and connected to said valve member, such that said rotary plate and thus said valve member are indirectly rotated by said magnet due to the magnetic force thereof.

4. A gas analyzer as claimed in claim 1, wherein said rotary valve means comprises a cylindrical chamber defined by a cylindrical wall within said block, and a rotatable valve member extending into said chamber, said valve member having first opposite spaced walls contacting said cylindrical wall and second opposite spaced walls spaced from said cylindrical wall and defining therewith first and second connecting chambers, said first and second inlets comprise first and second passages within said block, said first and second outlets comprise third and fourth passages within said block, said first and second passages having inlet ends opening exterior of said block and outlet ends opening into said cylindrical wall, said third and fourth passages having first ends opening into said cylindrical wall and second ends connected to said first and second cells, whereby said valve member is rotatable between said first position, whereat said first connecting chamber connects said outlet end of said first passage with said first end of said third passage and said second connecting chamber connects said outlet end of said second passage with said first end of said fourth passage, and said second position, whereat said first connecting chamber connects said outlet end of said first passage with said first end of said fourth passage and said second connecting chamber connects said outlet end of said second passage with said first end of said third passage.

5. A gas analyzer as claimed in claim 1, wherein said block has therein first and second openings receiving therein said first and second cells.

* * * * *